United States Patent
Harris et al.

(10) Patent No.: US 6,589,278 B1
(45) Date of Patent: Jul. 8, 2003

(54) VASCULAR PROSTHESIS

(75) Inventors: Peter Lyon Harris, Liverpool (GB); Thien Voon How, Liverpool (GB)

(73) Assignee: IMPRA, Inc., Tempe, AZ (US)

( * ) Notice: Subject to any disclaimer, the term of this patent is extended or adjusted under 35 U.S.C. 154(b) by 0 days.

(21) Appl. No.: 09/762,761
(22) PCT Filed: May 15, 1998
(86) PCT No.: PCT/GB99/01418
  § 371 (c)(1),
  (2), (4) Date: Oct. 5, 2001
(87) PCT Pub. No.: WO98/52495
  PCT Pub. Date: Nov. 26, 1998

(30) Foreign Application Priority Data

May 17, 1997 (GB) .............................. 9709967

(51) Int. Cl.$^7$ .................................. A61F 2/06
(52) U.S. Cl. .................. 623/1.31; 623/1.3; 623/1.36
(58) Field of Search ................ 623/1.31, 1.53, 623/1.13, 1.4, 1.28, 1.35, 2.36, 1.54, 1.3, 1.1, 1.49, 1.36; 606/1.53; 128/334, 898

(56) References Cited

U.S. PATENT DOCUMENTS

| | | |
|---|---|---|
| 2,127,903 A | 8/1938 | Bowen |
| 3,196,194 A | 7/1965 | Ely, Jr. et al. |
| 3,683,926 A | 8/1972 | Suzuki |
| 3,818,511 A | 6/1974 | Goldberg et al. |
| 3,853,462 A | 12/1974 | Smith |
| 3,945,052 A | 3/1976 | Liebig |
| 3,986,828 A | 10/1976 | Hoffman, Jr. et al. |
| 4,047,252 A | 9/1977 | Liegib et al. |
| 4,234,535 A | 11/1980 | Okita |
| 4,309,776 A | 1/1982 | Berguer |
| 4,313,231 A | 2/1982 | Koyamada |
| 4,321,914 A | 3/1982 | Begovac et al. |
| 4,354,495 A | 10/1982 | Bodicky |
| 4,366,819 A * | 1/1983 | Kaster .................... 606/153 |

(List continued on next page.)

FOREIGN PATENT DOCUMENTS

| | | |
|---|---|---|
| EP | 0 269 254 A1 | 10/1987 |
| WO | WO 96/00103 | 1/1996 |
| WO | WO 97/31591 | 9/1997 |
| WO | WO 98/52495 | 11/1998 |

OTHER PUBLICATIONS

"Interposition Vein Patches for Vascular Reconstruction", pp. 1–3, J.F. Chester et al.
"The Use of The Vein Cuff and PTFE", Vascular Surgical Techniques, as Atlas, Second Edition, pp. 276–286, Justin H. Miller et al.
"Improved Technique for Polytetraflouroethylene Bypass Grafting: Long–Term Results Using Anastomotic Vein Patches", The British Journal of Surgery, 1992, vol. 79, Apr. 4, 1992, pp. 348–354, R.S. Taylor et al.
"Polytetraflouroethylene (PTFE) Femorodistal Bypass", Rob & Smith's Operative Surgery/Vascular Surgery Fifth Edition, pp. 330–340, John H. N. Wolfe.

*Primary Examiner*—Paul Prebilic
*Assistant Examiner*—Crystal M Gilpin
(74) *Attorney, Agent, or Firm*—Morrison & Foerster

(57) ABSTRACT

A vascular prosthesis (50) comprises a tube (52) of material other than autologous vascular tissue, the tube having an end formation for surgical connection direct to an opening formed in an artery, the formation comprising an enlarged chamber (54) having a heel (56) and a toe (58) at opposite ends of a first longer diameter parallel to the axis of the tube and a second shorter transverse diameter the enlarged chamber serving to promote localised movement of blood having a non-laminar nature with a shear stress inducing relationship to receiving arterial wall.

12 Claims, 3 Drawing Sheets

U.S. PATENT DOCUMENTS

| | | |
|---|---|---|
| 4,416,028 A | 11/1983 | Eriksson et al. |
| 4,441,215 A * | 4/1984 | Kaster ..................... 623/1.37 |
| 4,482,516 A | 11/1984 | Bowman et al. |
| 4,503,568 A | 3/1985 | Madras |
| 4,517,687 A | 5/1985 | Liebig et al. |
| 4,530,113 A | 7/1985 | Matterson |
| 4,601,718 A | 7/1986 | Possis et al. |
| 4,728,328 A | 3/1988 | Hughes et al. |
| 4,743,480 A | 5/1988 | Campbell et al. |
| 4,816,028 A | 3/1989 | Kapadia et al. |
| 4,840,940 A | 6/1989 | Sottiurai |
| 4,883,453 A | 11/1989 | Berry et al. |
| 4,909,979 A | 3/1990 | Possis et al. |
| 4,957,508 A | 9/1990 | Kaneko et al. |
| 5,100,422 A | 3/1992 | Berguer et al. |
| 5,110,526 A | 5/1992 | Hayashi et al. |
| 5,156,619 A | 10/1992 | Ehrenfeld |
| 5,376,110 A | 12/1994 | Tu et al. |
| 5,387,236 A | 2/1995 | Noishiki et al. |
| 5,399,352 A | 3/1995 | Hanson |
| 5,443,497 A * | 8/1995 | Venbrux ..................... 623/1.13 |
| 5,456,712 A | 10/1995 | Maginot |
| 5,456,714 A * | 10/1995 | Owen ..................... 623/1.31 |
| 5,653,743 A * | 8/1997 | Martin ..................... 623/1.35 |
| 5,695,504 A | 12/1997 | Gifford, III et al. |
| 5,849,036 A * | 12/1998 | Zarate ..................... 623/1.31 |
| 5,893,886 A | 4/1999 | Zegdi et al. |
| 6,019,788 A | 2/2000 | Butteres et al. |
| 6,136,022 A | 10/2000 | Nunez et al. |
| 6,187,033 B1 | 2/2001 | Schmitt et al. |
| 6,210,430 B1 | 4/2001 | Solem |
| 6,436,135 B1 | 8/2002 | Goldfarb |

\* cited by examiner

VASCULAR PROSTHESIS

This application is related to U.S. application Ser. No. 09/183,132, filed Oct. 30, 1998, which is a continuation of U.S. application Ser. No. 8/656,065, filed May 31, 1996, now U.S. Pat. No. 5,861,026, and claims the benefit of United Kingdom patent application GB 9709967.5, filed May 17, 1997, which applications are incorporated by reference.

CROSS-REFERENCE TO RELATED APPLICATIONS

This application claims priority to United Kingdom patent application GB 9709967.5, filed May 17, 1997, which was filed as International patent application PCT/GB98/01418 on May 15, 1998, and which was published as International publication WO 98/52495A1 on Nov. 26, 1998.

This invention concerns prosthetic grafts for use in vascular surgery, particularly for by-passes to relatively small arteries.

By-passes required to save limbs can be long, say going from groins to below knees, and to arteries that may be as small as 1 to 5 mm in diameter. Where patients have no other veins that can be used, as is often the case with patients having relevant serious conditions, the only positive alternative is to use prosthetic grafts of synthetic materials, for example flexible tubes of polytetrafluoroethylene (PIFE). Simple direct end connections or anastomosis of prosthetic graft tubes (usually run at an acute angle or more or less parallel with the artery and end cut at an angle) to side apertures in arteries, perhaps particularly arteries substantially less than 5 mm in diameter, has unfortunately been followed by formation of fibrous intimal hyperplasia, which leads to serious blood flow reduction and even stoppage. The fibrous intimal hyperplasia occurs in regions within and around the graft connection, where there is little or no shear stress between the blood flow and the graft and arterial walls.

It is known to use a small piece of natural vein to make a short cuff known as the Miller cuff, that is joined by surgical stitching to and between the artery opening and the end of the prosthetic graft tube. Improved success rates for indirect prosthesis-to-vein-to-artery connection, compared with direct prosthesis-to-artery, have involved reduced adverse effect from intimal hyperplasia. Contributory factors, for cuff type and other prosthesis types, have been considered and postulated as including reducing tendencies to turbulence of blood flow, and/or optimising approximation to laminar blood flow, and/or for suppleness of the natural vein parts to aid absorption or cushioning blood pulsing. These factors have further been seen particularly as contributing to avoiding or minimising occurrence of artery wall shear stress. However, fibrous intimal hyperplasia still occurs with the so called Miller cuff because regions of flow separation and low shear stress still occur within the cuff.

U.S. Pat. No. 5,156,619 discloses a vascular prosthesis comprising a tube of material other than autologous vascular tissue, the tube having an enlarged end formation for surgical connection direct to an opening formed in an artery, the formation having a heel and a toe at opposite ends of a first longer diameter parallel to the axis of the tube and a second shorter transverse diameter.

WO-A-9731591 discloses a flanged graft for end-to-side anastomosis grafting having an integral terminal flanged skirt or cuff, which facilitates an end-to-side anastomosis directly between an artery and the expanded flange bypass graft without need for an intervening venous collar or venous patch.

It has been proposed to provide a vascular prosthesis comprising a tube of synthetic material having an end formation for surgical connection directly to an opening formed in an artery, the end formation comprising an enlarged chamber serving to promote localised movement of blood having a non-laminar nature with a shear stress inducing relationship to the arterial wall. The enlarged chamber has a convex outer wall. Further experimentation has revealed that this type of vascular prosthesis, whilst representing an improvement on the Miller cuff is still not ideal.

An object of this invention is to provide an improved vascular prosthesis for use in vascular surgery.

According to the present invention there is provided a vascular prosthesis comprising a tube of material other than autologous vascular tissue, said tube having an end formation for surgical connection direct to an opening formed in an artery, said formation comprising an enlarged chamber having a heel and a toe at opposite ends of a first longer diameter parallel to the axis of the tube and a second shorter transverse diameter, characterised in that transition between the tube and the toe is outwardly initially convex before a final concave portion (64), whereby said enlarged chamber serves to promote localised movement of blood having a non-laminar nature with shear stress inducing relationship to receiving arterial wall.

The heel of the enlarged chamber is formed at one end of the longer diameter, and the transition between the tube and the heel is preferably generally concave.

Transition between the tube and opposite ends of the shorter diameter is preferably outwardly convex.

It is also preferable that the tube have a narrower portion prior to transition to the enlarged chamber. It is believed that such narrowing of the tube will increase blood velocity entering the enlarged chamber of the prosthesis and hence increase shear stress in that region. The vascular prosthesis of the invention is intended to promote vertical blood flow in the region of its arterial connection in order to reduce or eliminate regions of low shear stress and regions of long residence times where blood elements can accumulate in the region of the graft connection.

The grafts of the invention are preferably made of plastics material, especially polytetrafluoroethylene (PTFE).

The term "non-laminar" as used herein is intended to define blood flow other than parallel to arterial walls and, in particular, includes localised laminar movement of blood having significant secondary components.

Separation of flowing blood from the inner wall of the tube near its enlarged chamber, and associated with non-laminar flow, is preferably such as to produce a swirling action that may include locally circulatory or recirculatory movement of blood, further preferably in the nature of or including a vortex action. Such blood flow separation will usually be at and adjacent preferred acute angling of the prosthesis tube for its direct connection to the artery, say at least partially within the enlarged chamber.

A preferred end chamber of the prosthesis tube of the invention is an enlargement which produces blood flow characteristics therein that result in an increase in wall shear stress.

Desired non-laminar blood flow promotion is preferably effective only in phases of cycles of blood-flow pulsing, which phases preferably alternate with other phases of more laminar flow sufficient to assist flow of all blood into the artery away and from that end of the prosthesis. The pulsed nature of normal blood flow involved successive time-spaced rises in pressure. Each pressure rise preferably causes both an initial relatively smooth or laminar blood flow in and out of the prosthesis-to-artery connection and a later transition into desired non-laminar blood movement. The preferred non-laminar vortex type movement preferably collapses before the next pressure rise.

This invention will now be further described, by way of example only, with reference to the accompanying drawings, in which:

FIG. 1 is an idealised sectional line diagram useful for explaining, problems arising from simple direct connection or anastomoses of a prosthetic graft tube 10 of synthetic material to an opening made in an artery 12;

FIG. 2 shows use of a veinous cuff 34 interposed between a prosthetic graft tube 30 and an artery 32;

Figure 1:
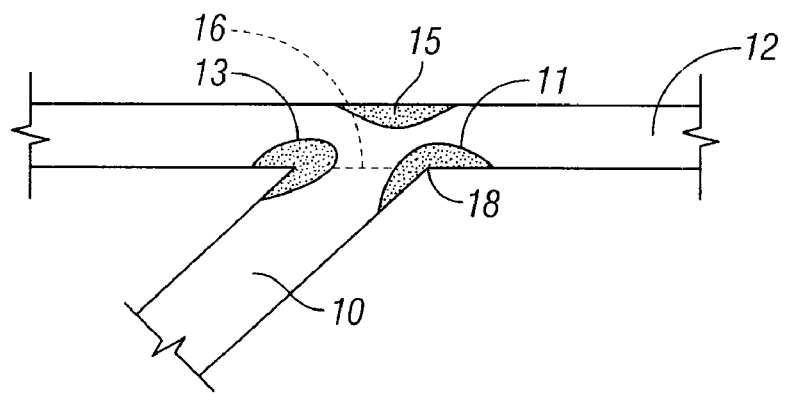

In the drawings, referring first to FIG. 1, artery 12 has an opening made by an incision at 16. Prosthetic graft tube 10 of synthetic material (for which PTFE, most usually ePTFE, is widely used in practice) is run at an acute angle or more or less parallel to the artery 12. Tube 10 is indicated cut to an angled end 18 that is end to edge sewn into the opening 16. Unfortunately, there is a tendency for myointimalhyperplasia to occur later in the receiving artery 12, see indicated development of fibrous or scare-like tissue in the toe and heel positions 11 and 13, respectively, and also at plate position 15 opposite the opening 16. This development can seriously reduce the very blood flow that it is the object of the procedure to improve. Indeed, this condition all to often progresses to blocking of such blood flow altogether. These problems are all the greater the smaller the calibre of the receiving artery 12, which can be as small as 1 to 5 mm for the type of distal by-passes often needed, say to go from the groin to beyond the knee as is frequently necessary to save a patient's lower leg.

Figure 2:
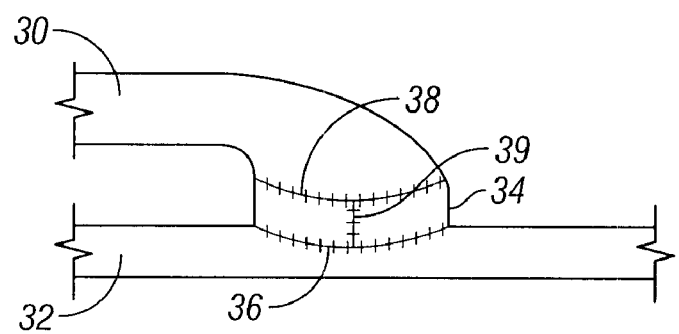
Figure 3:
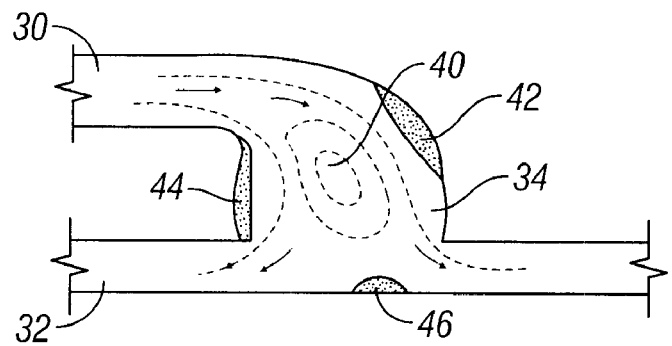
FIG. 3 is a section through the graft of FIG. 2 showing typical blood flow therethrough.
Figure 4:
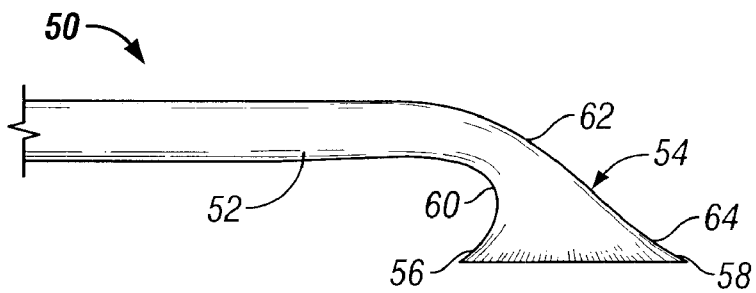
FIG. 4 is a side view of a first prosthetic graft of the invention.
Figure 5:
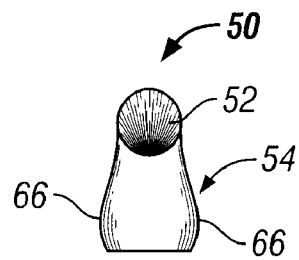
FIG. 5 is a rear view of the graft of FIG. 4.
Figure 6:
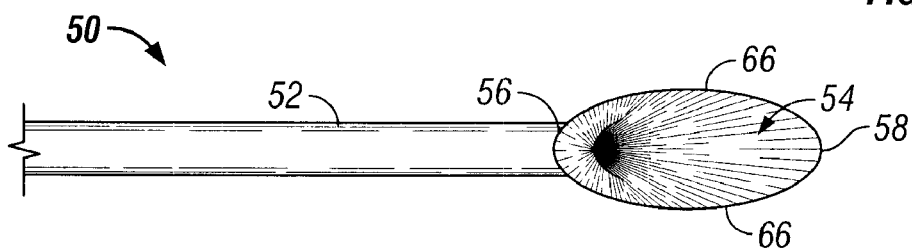
FIG. 6 is a view from below of the graft of FIG. 4.
Figure 7:
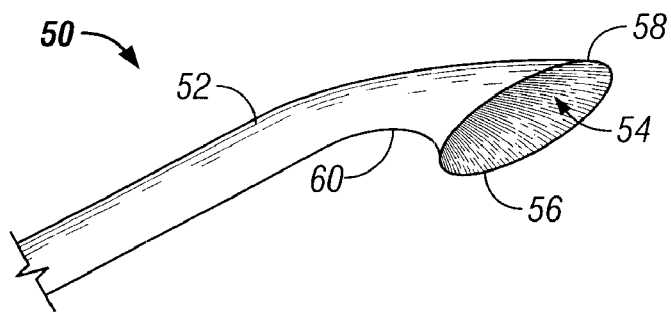
FIG. 7 is a perspective view of the graft of FIG. 4.
Figure 8:
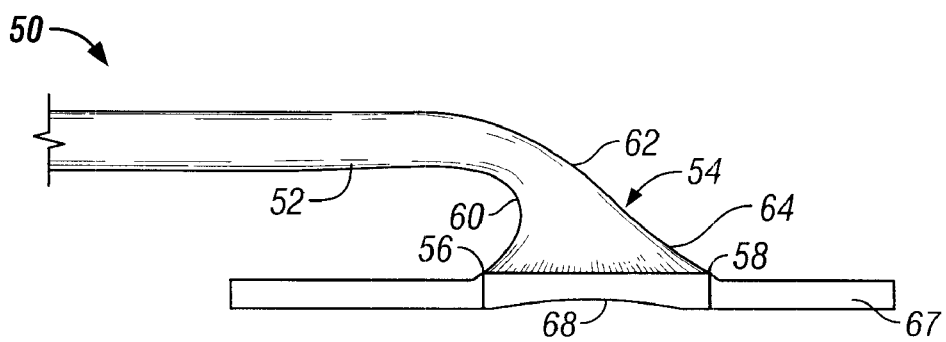
FIG. 8 shows the graft of FIGS. 4 to 7 connected to an artery.
Figure 9:
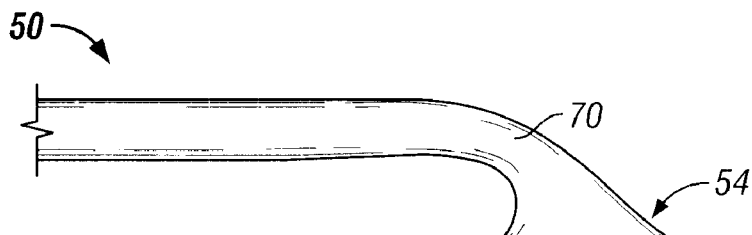
FIG. 9 is a side view of a second prosthetic graft of the invention.
Figure 10:
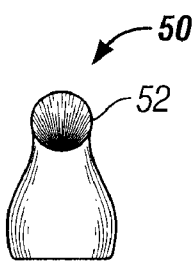
FIG. 10 is a rear view of the graft of FIG. 9.
Figure 11:
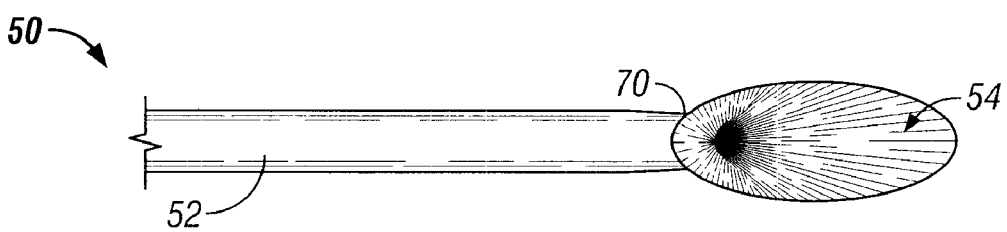
FIG. 11 is a view from below of the graft of FIG. 9.
Figure 12:
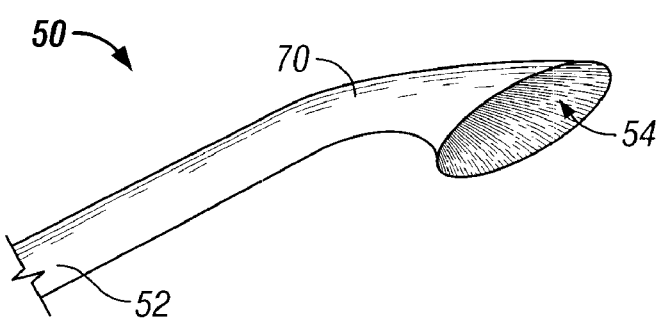
FIG. 12 is a perspective view of the graft of FIG. 9.
Figure 13:
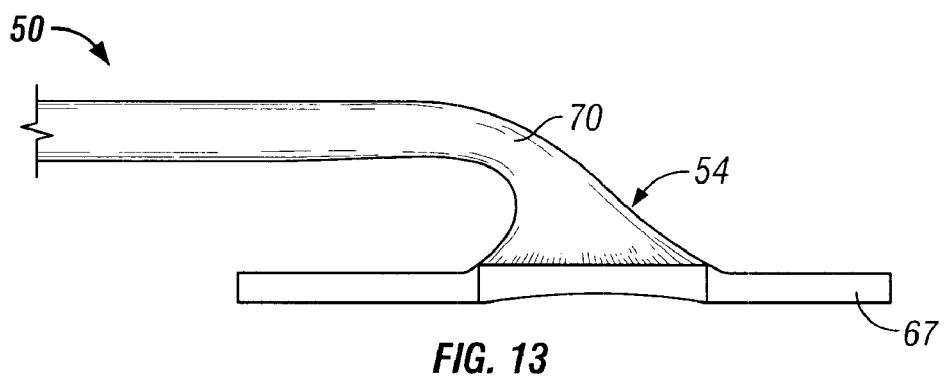
FIG. 13 shows the graft of FIGS. 9 to 12.

FIGS. 2 and 3 of the drawings illustrate the Miller cuff, aimed at reducing such problems takes a short length of other vein, usually from still usable parts of the saphenous vein that would be used in its entirety if serviceable. This short length of autologous vein, typically 2 to 3 mm in diameter, is removed and opened along its length, then sutured first to an opening 36 of the artery 32 and end-to-end to itself, see 39. The completed cuff 34 is trimmed and anastomoses completed, at 38 to normally wider prosthetic graft tube 30. The graft tube 20 is typically of PTFE and at least 4 mm, preferably 6mm if not more, in diameter. Improvement in terms of reducing development of intimal hyperplasia was originally, and has since consistently been, attributed to the autologous vein-to-artery junction. The suppleness of the veinous tissue may also have contributed to this improvement by assisting absorption of pressure pulsing and reducing shear wall stress in the receiving artery. Wall shear stress was assumed and reported as being the major causative factor in development of intimal hyperplasia. This procedure has become popular and has been the subject of considerable development, including to use in a compared manner relative to interconnected small arteries.

Typical blood flow through the Miller cuff as shown in FIG. 3. A vortex 40 is formed to increase shear stress but at opposite sides of the cuff low shear stress regions 42, 44 occur where accumulation of deposits can occur resulting in intimal hyperplasia. Furthermore where flow separates at the arterial wall opposite the cuff, a low shear stress region 46 also occurs where intimal hyperplasia is possible.

Turning to FIGS. 4 to 8 of the accompanying drawings a first vascular prosthetic graft 50 according to the invention is ideally made of polytetrafluoroethylene. The graft has a tubular part 52 of any desired length according to the length of the by-pass to be made using the graft and an enlargement 54 at one or both ends of the tube 52 (only one is shown). The enlargement 54 has an open end of a generally oval cross-section forming a heel 56 and a toe 58 at opposite ends of the larger diameter of the open end.

There is a generally outwardly concave transition 60 between the tube 52 and the heel 56 and between the tube 52 and the toe 58 a firstly convex (62) and a final concave (64) transition.

Sides 66 of the enlargement at opposite ends of the shorter diameter of the open end are generally outwardly convex.

The plane of the open end of the enlargement and of the tube 52 are generally parallel but it should be noted that prosthetic grafts having different separations thereof may be made for use in different situations. It should be further noted that prosthetic grafts having open ends of varying longer diameters may be produced. Furthermore, the degree of curvature either to the heel or the toe may be varied from graft to graft, in order to alter blood flow characteristics through the graft connection.

The prosthetic graft 50 is in practice connected to an artery by forming a slit a side of an artery 67, opening out the slit and stitching the open end of the graft to the sides of the slit. It is to be noted that such connection of the graft causes the artery to have a concave underside opposite the graft as can be seen at 68 in FIG. 8 of the drawings.

The length of the open end of the graft will probably be in the order of 14 to 36 mm and the width of the open end is unlikely to be less than 6 mm and probably not greater than 14 mm.

FIGS. 9 to 13 illustrate a variation on the prosthetic graft of the persons embodiment. Like parts have been numbered similarly and only the main difference between them will now be described. In order to increase the velocity of blood flow through the graft connection to an artery, the tube 52 of the graft includes a narrower portion 70 prior to commencement of the enlargement.

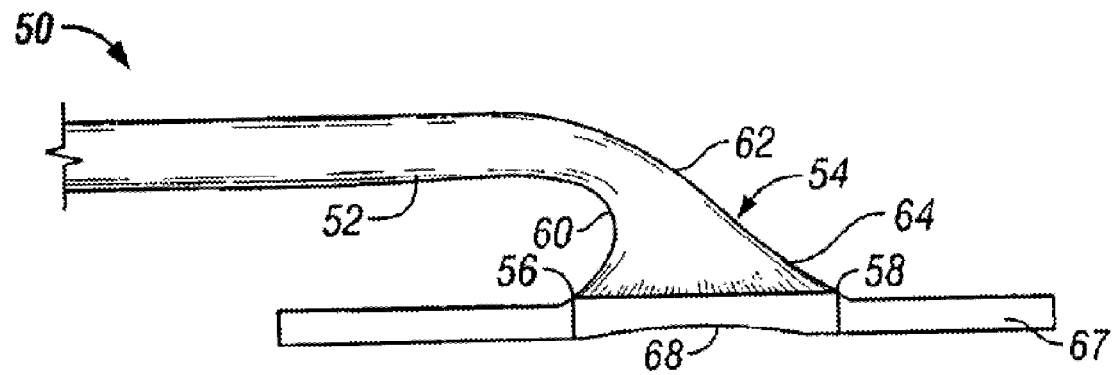

What is claimed is:

1. A vascular prosthesis, comprising a tube of material other than autologous vascular tissue, said tube having an end formation configured for surgical connection to an opening formed in a blood vessel, said end formation comprising an enlarged chamber having a first diameter parallel to the axis of the tube and a second diameter transverse to the axis of the tube, wherein said first diameter is longer than said second diameter, said first diameter comprising a heel and a toe, wherein a transition between said tube and said toe is outwardly initially convex before a final concave portion, and wherein said enlarged chamber is adapted to induce a concave section in said blood vessel upon attachment of said prosthesis thereto.

2. The vascular prosthesis according to claim 1, wherein said enlarged chamber is configured to promote localized movement of blood having a non-laminar nature with a shear stress inducing relationship to a wall of said blood vessel.

3. The vascular prosthesis according to claim 1, wherein a transition between said tube and said heel is generally outwardly concave.

4. The vascular prosthesis according to claim 1, wherein opposing sides of said second diameter are generally outwardly convex.

5. The vascular prosthesis according to claim 1, further comprising a narrow section positioned between said tube and said end formation, wherein a diameter of said narrow section is less than a diameter of said tube.

6. The vascular prosthesis according to claim 1, said tube having a second end formation at an end of said tube opposite said end formation.

7. The vascular prosthesis according to claim 6, wherein said second end formation comprises a second enlarged chamber having a first diameter parallel to the axis of the tube and a second diameter transverse to the axis of the tube, wherein said first diameter is longer than said second diameter, said first diameter comprising a heel and a toe, wherein a transition between said tube and said toe is outwardly initially convex before a final concave portion.

8. The vascular prosthesis according to claim 7, wherein a transition between said tube and said heel of said second enlarged chamber is generally outwardly concave.

9. The vascular prosthesis according to claim 7, wherein opposing sides of said second diameter of said second enlarged chamber are generally outwardly convex.

10. The vascular prosthesis according to claim 7, further comprising a second narrow section positioned between said tube and said second end formation, wherein a diameter of said second narrow section is less than a diameter of said tube.

11. The vascular prosthesis according to claim 1, wherein said first diameter is between approximately 14 and 36 mm and said second diameter is no greater than approximately 14 mm.

12. A method in vascular by-pass procedures for producing a concave section in a second side of a blood vessel, wherein a first side of the blood vessel is attached to a prosthesis, comprising:

forming a slit in the first side of the blood vessel, creating an opening therein; and attaching the prosthesis of claim 1 to said opening.

* * * * *

UNITED STATES PATENT AND TRADEMARK OFFICE
CERTIFICATE OF CORRECTION

PATENT NO. : 6,589,278 B1
APPLICATION NO. : 09/762761
DATED : July 8, 2003
INVENTOR(S) : Harris et al.

It is certified that error appears in the above-identified patent and that said Letters Patent is hereby corrected as shown below:

The title page : Please delete entire patent title page.

And insert title page, as attached

Signed and Sealed this

Twenty-sixth Day of August, 2008

JON W. DUDAS
*Director of the United States Patent and Trademark Office*

United States Patent
Harris et al.

(10) Patent No.: US 6,589,278 B1
(45) Date of Patent: Jul. 8, 2003

(54) VASCULAR PROSTHESIS

(75) Inventors: Peter Lyon Harris, Liverpool (GB); Thien Voon How, Liverpool (GB)

(73) Assignee: IMPRA, Inc., Tempe, AZ (US)

(*) Notice: Subject to any disclaimer, the term of this patent is extended or adjusted under 35 U.S.C. 154(b) by 0 days.

(21) Appl. No.: 09/762,761
(22) PCT Filed: May 15, 1998
(86) PCT No.: PCT/GB99/01418
§ 371 (c)(1),
(2), (4) Date: Oct. 5, 2001
(87) PCT Pub. No.: WO98/52495
PCT Pub. Date: Nov. 26, 1998

(30) Foreign Application Priority Data

May 17, 1997 (GB) .................................. 9709967

(51) Int. Cl.⁷ .................................. A61F 2/06
(52) U.S. Cl. .................. 623/1.31; 623/1.3; 623/1.36
(58) Field of Search ................... 623/1.31, 1.53, 623/1.13, 1.4, 1.28, 1.35, 2.36, 1.54, 1.3, 1.1, 1.49, 1.36; 606/1.53; 128/334, 898

(56) References Cited

U.S. PATENT DOCUMENTS

| | | |
|---|---|---|
| 2,127,903 A | 8/1938 | Bowen |
| 3,196,194 A | 7/1965 | Ely, Jr. et al. |
| 3,683,926 A | 8/1972 | Suzuki |
| 3,818,511 A | 6/1974 | Goldberg et al. |
| 3,853,462 A | 12/1974 | Smith |
| 3,945,052 A | 3/1976 | Liebig |
| 3,986,828 A | 10/1976 | Hoffman, Jr. et al. |
| 4,047,252 A | 9/1977 | Liegib et al. |
| 4,234,535 A | 11/1980 | Okita |
| 4,309,776 A | 1/1982 | Berguer |
| 4,313,231 A | 2/1982 | Koyamada |
| 4,321,914 A | 3/1982 | Begovac et al. |
| 4,354,495 A | 10/1982 | Bodicky |
| 4,366,819 A * | 1/1983 | Kaster .................. 606/153 |

(List continued on next page.)

FOREIGN PATENT DOCUMENTS

| | | |
|---|---|---|
| EP | 0 269 254 A1 | 10/1987 |
| WO | WO 96/00103 | 1/1996 |
| WO | WO 97/31591 | 9/1997 |
| WO | WO 98/52495 | 11/1998 |

OTHER PUBLICATIONS

"Interposition Vein Patches for Vascular Reconstruction", pp. 1–3, J.F. Chester et al.
"The Use of The Vein Cuff and PTFE", Vascular Surgical Techniques, as Atlas, Second Edition, pp. 276–286, Justin H. Miller et al.
"Improved Technique for Polytetraflouroethylene Bypass Grafting: Long–Term Results Using Anastomotic Vein Patches", The British Journal of Surgery, 1992, vol. 79, Apr. 4, 1992, pp. 348–354, R.S. Taylor et al.
"Polytetraflouroethylene (PTFE) Femorodistal Bypass", Rob & Smith's Operative Surgery/Vascular Surgery Fifth Edition, pp. 330–340, John H. N. Wolfe.

Primary Examiner—Paul Prebilic
Assistant Examiner—Crystal M Gilpin
(74) Attorney, Agent, or Firm—Morrison & Foerster

(57) ABSTRACT

A vascular prosthesis comprises a tube of material other than autologous vascular tissue, the tube having an end formation for surgical connection direct to an opening formed in an artery, the formation comprising an enlarged chamber having a heel and a toe at opposite ends of a first longer diameter parallel to the axis of the tube and a second shorter transverse diameter the enlarged chamber serving to promote localised movement of blood having a non-laminar nature with a shear stress inducing relationship to receiving arterial wall.

12 Claims, 3 Drawing Sheets